United States Patent [19]

Robertson et al.

[11] 4,308,214

[45] Dec. 29, 1981

[54] PREPARATION OF DIALKYLDITHIOPHOSPHINATES

[75] Inventors: Allan J. Robertson, Thorold; Tony Ozog, Welland, both of Canada

[73] Assignee: Cyanamid Canada Inc., Ontario, Canada

[21] Appl. No.: 232,102

[22] Filed: Feb. 6, 1981

[51] Int. Cl.³ .............................................. C07F 9/30
[52] U.S. Cl. ............................................. 260/502.4 R
[58] Field of Search ................................. 260/502.4 R

[56] References Cited

U.S. PATENT DOCUMENTS 3,238,248   3/1960   Rauhut ........................ 260/502.4 R Primary Examiner—Joseph E. Evans
Attorney, Agent, or Firm—Paul W. Leuzzi, II

[57] ABSTRACT

Dialkylphosphine is added to a mixture of sulfur and water at 50°–90° C. After approximately 25% of the dialkylphosphine is charged, an alkali, such a sodium hydroxide, is added to neutralize the dialkyldithiophosphinic acid that forms. At this elevated temperature the neutralization reaction proceeds rapidly thereby preventing any alkali from reacting with the sulfur to form sulfides. Dialkyldithiophosphinate yields from this process are on the order of about 95–98%.

10 Claims, No Drawings

PREPARATION OF DIALKYLDITHIOPHOSPHINATES

BACKGROUND OF THE INVENTION

The present invention relates to a new and useful method of preparing organophosphorous compounds. More particularly, the present invention relates to a method of preparing dialkyldithiophosphinates.

As is known, middling particles which result from either coarse grinding or from intimate association of the component minerals which make up an ore and frequently exist even after fine grinding are composed of two or more mineral species. In general, such polyphase particles are generally more difficult to concentrate by flotation than free mineral grains. In some free-milling ores, the values are readily separated from the gangue by crushing and grinding to permit the application of flotation techniques. In other ores a middling treatment problem is presented. The extractive metallurgist is thus compelled to compromise between obtaining a desired high recovery of mineral values and the grade of the concentrate produced. High recoveries in concentrates of low grade entail high treatment costs in subsequent upgrading and refining operations, which may force the rejection of larger percentages of the contained metal values so as to obtain a concentrate which is salable or amenable to further treatments. Further, in many cases, the middling particles are not recovered, even though amenable to standard refining processes, and thus represent high losses of the desired mineral values.

Dialkyldithiophosphinates are effective promotors in solving the middling treatment problem of sulfide ores (See U.S. Pat. No. 3,355,017). These promotors were reported therein to be more effective than known collectors usually employed in floating coarse mineral particles, particularly particles in the plus 150 Tyler mesh range.

Dialkyldithiophosphinates useful as sulfide mineral promoters conventionally are prepared by reacting dialkylphosphine with a mixture of water, sulfur and base, such as sodium hydroxide. Although the prior art discloses reaction temperatures up to about 100° C., commercial considerations dictate that temperatures less than 30° C. be employed (see U.S. Pat. No. 3,238,248). These low temperature reactions have resulted in yields in the range of about 75-80% and are extremely slow due to the depressed temperature at which the reaction proceeds. Elevation of the temperature of the conventional reaction produces a side reaction between the sodium hydroxide and the sulfur resulting in undesirable alkali sulfides. The presence of alkali sulfide has several detrimental effects on the product and its application as a flotation promoter. In the product, alkali sulfides represent a yield loss of alkali and sulfur, produce an off-color solution and create a strongly disagreeable odor. In the application, alkali sulfides depress sulfide minerals during the flotation process and lead to a loss in recovery of those minerals.

Accordingly, there exists the need for an improved process for preparing dialkyldithiophosphinates. Such a new process should be capable of proceeding rapidly and yet maintain low levels of alkali sulfides so as to provide the highest yields and most effective flotation promoters.

SUMMARY OF THE INVENTION

The present invention provides a novel process for the preparation of dialkyldithiophosphinates. The process comprises the addition of dialkylphosphine to a mixture of sulfur and water at a temperature within the range of about 50° to 90° C., upon charging approximately 25% of the dialkylphosphine, an alkali is added to neutralize any dialkyldithiophosphinic acid that has formed. The elevated temperature results in a rapid neutralization reaction thereby preventing any appreciable amount of alkali sulfide from forming as a result of the side reaction between the alkali and the sulfur. The process results in yields on the order of about 95-98%.

DETAILED DESCRIPTION OF THE INVENTION

In accordance with the present invention, there is provided a process for the preparation of dialkyldithiophosphinates. The process involves heating a mixture of sulfur and water to between about 50° and 90° C., preferably 60°-75° C. since the yield begins to drop off around 80° C. To this heated mixture there is added dialkylphosphine. When between 10 to 50 percent of the dialkylphosphine has been charged, an alkali is then mixed in to neutralize the dialkyldithiophosphinic acid that forms. With less than 10% of the dialkylphosphine charged the alkali reacts with the sulfur to form unwanted alkali sulfides while with more than 50% of the dialkylphosphine charged the alkali neutralization reaction proceeds at a later time and thus unnecessarily prolongs the process of dialkyldithiophosphinate preparation. Although a charge of the dialkylphosphine between about 10%-50% is considered an effective range, it is preferred that the alkali be added at a charge of between about 20 and 30% of the dialkylphosphine to optimize the process.

Suitable dialkylphosphines include those dialkylphosphines wherein the alkyl radicals individually contain from two to twelve carbon atoms, inclusive, preferably from three to six carbon atoms, inclusive. These alkyl groups may be straight or branched chained or cyclic. The straight chain primary olefins, from which most dialkylphosphines are made, are generally the cheapest and most readily available starting materials. Although the branched chain olefins are more expensive, in general they have produced stronger dialkylphosphine promoters for the flotation of sulfide minerals and thus may justify the use of these olefins in their preparation. Cyclic olefins containing cyclohexyl and cyclooctyl groups are also considered effective starting materials for the dialkylphosphine. The dialkylphosphine may contain either saturated or unsaturated alkyl groups; however, experience has shown that it is much more difficult to prepare the unsaturated dialkylphosphines in good yield.

The dialkylphosphine employed in the preparation process may contain small amounts of monoalkylphosphine and trialkylphosphine. The monoalkylphosphine will ultimately form a sodium monoalkylphosphonate impurity in the final solution whereas the trialkylphosphine will form trialkylphosphinesulfide. The trialkylphosphinesulfide will either remain in solution as an impurity or precipitate out. In the latter case, it can be removed by filtration or centrifugation along with the unreacted sulfur.

Suitable alkalis useful in the instant process include, but are not limited to, the alkali hydroxides of sodium, lithium, potassium, rubidium and cesium; the alkali carbonates of these metals; and ammonium hydroxide. The preferred alkali, however, is sodium hydroxide. The alkali itself may be added in solid, pellet, powder, flake or solution form with the preferred form being a 50% solution of the alkali since this form is generally the most practical to handle and is available in drum and tank loads.

The reactants in the various reactions contemplated herein are generally present in stoichiometric quantities, although substantially greater than the stoichiometric amounts are suitable without upsetting the nature of the reaction whereas less than the stoichiometric amount of alkali or sulfur will result in a yield loss and ineffective promoters for sulfide minerals. It should be noted, however, that it is preferable to add a 5% molar excess of the sulfur to compensate for any impurities in the dialkylphosphine.

While atmospheric pressures are desirable for this type of reaction, super- and sub-atmospheric pressures are compatible.

The following specific examples illustrate certain aspects of the present invention, and, more particularly, point out methods of evaluating the unique advantages of preparing dialkyldithiophosphinates in accordance with the instant process. However, the examples are set forth for illustration only and are not to be construed as limitations on the present invention except as set forth in the appended claims. All parts and percentages are by weight unless otherwise specified.

EXAMPLE 1

A mixture of 67.2 parts of sulfur and 172.8 parts of water is heated to a temperature of approximately 70° C. To this mixture there are steadily metered in 36.5 parts of diisobutylphosphine (25%). After the diisobutylphosphine has been metered in 109.5 additional parts of diisobutylphosphine are metered in at a constant rate such that within the time necessary to meter in the diisobutylphosphine, 80.0 parts of a 50% solution of sodium hydroxide are also metered in at a constant rate to the mixture to neutralize the diisobutyldithiophosphinic acid that forms.

Analysis of the final product indicates a 95% yield of sodium diisobutylphosphinate.

EXAMPLE 2

A mixture of 67.2 parts of sulfur and 172.8 parts of water is heated to a temperature of approximately 70° C. To this mixture there are steadily metered in 36.5 parts of di-n-butylphosphine. After the di-n-butylphosphine has been metered in, 109.5 additional parts of di-n-butylphosphine are metered in at a rate such that within the time necessary to meter in all of the di-n-butylphosphine, 80.0 parts of a 50% solution of sodium hydroxide are also metered in at a constant rate to neutralize the di-n-butyldithiophosphinic acid that forms.

Analysis of the final product indicates a yield of sodium di-n-butyldithiophosphinate substantially equivalent to the yield reported in Example 1.

EXAMPLE 3

A mixture of 67.2 parts of sulfur and 116.8 parts of water is heated to a temperature of approximately 70° C. To this mixture there are steadily metered in 22.5 parts of diethylphosphine. After the diethylphosphine has been metered in, 67.5 additional parts of diethylphosphine are metered in at a rate such that within the time necessary to meter in all of the diethylphosphine, 80.0 parts of a 50% solution of sodium hydroxide are also metered in at a constant rate to neutralize the diethyl dithiophosphinic acid that forms.

Analysis of the final product indicates a yield of sodium diethyldithiophosphinate substantially equivalent to the yield reported in Example 1.

EXAMPLE 4

A mixture of 67.2 parts of sulfur and 114.8 parts of water is heated to a temperature of approximately 70° C. To this mixture there are steadily metered in 29.5 parts of dipropylphosphine. After the dipropylphosphine has been metered in, 88.5 additional parts of dipropylphosphine are metered in at a rate such that within the time necessary to meter in all of the dipropylphosphine, 80.0 parts of a 50% solution of sodium hydroxide are also metered in at a constant rate to neutralize the dipropyl dithiophosphinic acid that forms.

Analysis of the final product indicates a yield of sodium dipropyldithiophosphinate substantially equivalent to the yield reported in Example 1.

EXAMPLE 5

A mixture of 67.2 parts of sulfur and 200.8 parts of water is heated to a temperature of approximately 70° C. To this mixture there is steadily metered in 43.5 parts of di-n-pentylphosphine. After the di-n-pentylphosphine has been metered in, 130.5 additional parts of di-n-pentylphosphine are metered in at a rate such that within the time necessary to meter in all of the di-n-dipentylphosphine, 80.0 parts of a 50% solution of sodium hydroxide are also metered in at a constant rate to neutralize the di-n-pentyl dithiophosphinic acid that forms.

Analysis of the final product indicates a yield of sodium di-n-pentyldithiophosphinate substantially equivalent to the yield reported in Example 1.

EXAMPLE 6

A mixture of 67.2 parts of sulfur and 228.8 parts of water is heated to a temperature of approximately 70° C. To this mixture there are steadily metered in 50.5 parts of dihexylphosphine. After the dihexylphosphine has been metered in, 151.5 additional parts of dihexylphosphine are metered in at a rate such that within the time necessary to meter in all of the dihexylphosphine, 80.0 parts of a 50% solution of sodium hydroxide are also metered in at a constant rate to neutralize the dihexyl dithiophosphinic acid that forms.

Analysis of the final product indicates a yield of sodium dihexyldithiophosphinate substantially equivalent to the yield reported in Example 1.

EXAMPLE 7

A mixture of 67.2 parts of sulfur and 256.8 parts of water is heated to a temperature of approximately 70° C. To this mixture there are steadily metered in 57.5 parts of diheptylphosphine. After the diheptylphosphine has been metered in, 172.5 additional parts of diheptylphosphine are metered in at a rate such that within the time necessary to meter in all of the diheptylphosphine, 80.0 parts of a 50% solution of sodium hydroxide are also metered in at a constant rate to neutralize the diheptyl dithiophosphinic acid that forms.

Analysis of the final product indicates a yield of sodium diheptyldithiophosphinate substantially equivalent to the yield reported in Example 1.

EXAMPLE 8

A mixture of 67.2 parts of sulfur and 284.8 parts of water is heated to a temperature of approximately 70° C. To this mixture there are steadily metered in 64.5 parts of di-n-octylphosphine. After the di-n-octylphosphine has been metered in, 193.5 additional parts of di-n-octylphosphine are metered in at a rate such that within the time necessary to meter in all of the di-n-octylphosphine, 80.8 parts of a 50% solution of sodium hydroxide are also metered in at a constant rate to neutralize the di-n-octyl dithiophosphinic acid that forms.

Analysis of the final product indicates a yield of sodium di-n-octyldithiophosphinate substantially equivalent to the yield reported in Example 1.

EXAMPLE 9

When the procedure of Example 1 is followed in every material detail except that dicyclohexylphosphine and ammonium hydroxide are substituted in place of the diisobutylphosphine and sodium hydroxide respectively, and the ammonium hydroxide is charged after about 12% of the dicyclohexylphosphine is added, a dicyclohexyldithiophosphinate is obtained in substantially equivalent yield to the diisobutyldithiophosphinate of Example 1.

EXAMPLE 10

When the procedure of Example 1 is followed in every material detail except that di-2-butyl-propylphosphine and potassium hydroxide are substituted in place of the diisobutylphosphine and sodium hydroxide respectively and the potassium hydroxide is charged after about 45% of the di-2-butyl-propylphosphine is added, a di-2-butyl-propyldithiophosphinate is obtained in substantially equivalent yield to the diisobutyldithiophosphinate of Example 1.

EXAMPLE 11

A sample of chalcopyrite ore is wet ground to 60% −200 mesh in a rod mill. Lime is added to the ore sample to adjust the pH to 10.5. The ground ore sample is next charged into a flotation cell, maintaining the pH of 10.5 with lime water. To the cell 0.04 pound of the sodium diisobutyldithiophosphinate prepared in Example 1 is added per ton of ground ore. The ore is conditioned for four (4) minutes and thereafter 0.05 pound of methylisobutylcarbinol (MIBC) per ton of ground ore is added. The ore is again allowed to condition, this time for one (1) minute. An impeller speed of 1500 rpm is set and the copper rougher concentrate is collected for four (4) minutes. Results are reported in Table I.

COMPARATIVE EXAMPLES A & B

The procedure of Example 11 is followed in every material detail except that in place of sodium diisobutyldithiophosphinate there is employed sodium isobutylxanthate and sodium di-sec-butyldithiophosphate, respectively. Test results are given in Table I.

TABLE I

COPPER FLOTATION FROM CHALCOPYRITE ORE

| Example | Promoter Type | Dosage (lb/ton) | Concentrate Wt. % | Assays - % Cu Heads | Conc. | Tails | % Cu Recovery |
|---|---|---|---|---|---|---|---|
| 11 | Sodium diisobutyl-dithiophosphinate | 0.04 | 5.00 | 0.671 | 11.6 | 0.096 | 86.4 |
| Comparative A | Sodium isobutyl-xanthate | 0.04 | 6.63 | 0.671 | 8.62 | 0.107 | 85.1 |
| Comparative B | Sodium di-sec-butyldithiophosphate | 0.04 | 4.68 | 0.674 | 12.1 | 0.113 | 84.0 |

We claim:

1. A process for the preparation of dialkyldithiophosphinate comprising:
   (a) heating a mixture of sulfur and water to about 50° to 90° C.;
   (b) adding to the heated mixture about 10% to 50% of a charge of a dialkylphosphine at a continuous rate; and
   (c) adding to the heated mixture containing the charge of dialkylphosphine an alkali at a continuous rate while at the same time adding the remaining 50% to 90% of the charge of dialkylphosphine at a continuous rate wherein said continuous rates are such that the alkali acts to neutralize the dialkyldithiophosphinic acid formed during the reaction.

2. The process of claim 1 wherein the reaction mixture is maintained at a temperature of about 60° to 75° C.

3. The process of claim 1 wherein the amount of dialkylphosphine added to the reaction mixture prior to the alkali is about 20 to 30%.

4. The process of claim 1 wherein the alkali is an alkali hydroxide.

5. The process of claim 4 wherein the alkali is a 50% solution of sodium hydroxide.

6. The process of claim 1 wherein the dialkylphosphine employed has alkyl groups containing from two to twelve carbon atoms, inclusive.

7. The process of claim 6 wherein the dialkylphosphine employed has alkyl groups containing from three to six carbon atoms, inclusive.

8. The process of claim 7 wherein the dialkylphosphine is diisobutylphosphine.

9. The process of claim 7 wherein the dialkylphosphine is di-n-butylphosphine.

10. The process of claim 7 wherein the dialkylphosphine is dipentylphosphine.

* * * * *